United States Patent [19]

Prater et al.

[11] 4,117,248

[45] Sep. 26, 1978

[54] CONTINUOUS, LOW PRESSURE ETHYNYLATION PROCESS FOR THE PRODUCTION OF BUTYNEDIOL

[75] Inventors: J. Lewis Prater, Calvert City, Ky.; Robert L. Hedworth, Kinnelon, N.J.

[73] Assignee: GAF Corporation, New York, N.Y.

[21] Appl. No.: 792,349

[22] Filed: Apr. 29, 1977

[51] Int. Cl.² ............................................ C07C 29/00
[52] U.S. Cl. .................................................. 568/855
[58] Field of Search ..................... 260/635 Y; 568/855

[56] References Cited

U.S. PATENT DOCUMENTS

| 3,920,759 | 11/1975 | Hort | 260/635 Y |
| 4,002,694 | 1/1977 | Hort | 260/635 Y |

*Primary Examiner*—Joseph E. Evans

*Attorney, Agent, or Firm*—Walter C. Kehm; Walter Katz

[57] ABSTRACT

There is provided herein an improved, more continuous, low pressure ethynylation process for the production of butynediol which comprises first continuously reacting formaldehyde and acetylene in a reaction zone at low pressures, in a stirred aqueous medium, in the presence of a finely-divided ethynylation catalyst, to form a reaction product mixture containing butynediol and catalyst slurry. Then the reaction product mixture is withdrawn and continuously and simultaneously filtered and concentrated to form two streams, a catalyst-free filtrate stream and a flowable, concentrated catalyst slurry stream, the latter being capable of immediate recycling to the reaction zone without further treatment. The filtrate stream containing the butynediol is available for purification and further operations.

18 Claims, 2 Drawing Figures

CONTINUOUS, LOW PRESSURE ETHYNYLATION PROCESS FOR THE PRODUCTION OF BUTYNEDIOL

BACKGROUND OF THE INVENTION

1. Field of the Invention

This invention relates to an improved continuous, low pressure ethynylation process for the production of butynediol.

2. Description of the Prior Art

Butynediol has been prepared in the past by an ethynylation reaction in which formaldehyde and acetylene are reacted in the presence of an ethynylation catalyst. Such processes are described, for example, in U.S. Pat. Nos. 2,232,867, 2,300,969, 2,487,069, 2,712,560, 2,768,215, 3,108,140, 3,294,849, 3,560,576, 3,920,759 and Ger. DAS No. 2,206,693.

The ethynylation reaction generally employs some form of complex cuprous acetylide catalyst, either supported or unsupported, which catalyst may be generated or made active by a variety of methods and from a variety of copper compounds. Often the complex cuprous acetylide catalysts are used together with a bismuth compound to minimize undesired cuprene formation, cuprene being a product resulting from undesired actylene polymerization. The precursor material of the supported catalysts customarily used in the manufacture of butynediol are produced by impregnating the support with solutions of cupric and bismuth salts, such as the nitrates, drying, and calcining to produce the corresponding metal oxides. The cupric oxide thereafter is converted to the active complex cuprous acetylide catalyst in situ by suitable treatment with acetylene and formaldehyde.

In U.S. Pat. No. 3,920,759, a low pressure ethynylation process is described which utilizes as a catalyst an aqueous slurry of finely-divided complex cuprous acetylide supported on a magnesium silicate carrier, under intense agitation, to provide butynediol at a high rate of production under safe conditions. Nevertheless, it would be advantageous to provide an improved, and particularly a more continuous low pressure process, of the type described in U.S. Pat. No. 3,920,759, specifically with respect to the means by which the butynediol product may be separated from the catalyst slurry as a catalyst-free clear liquid stream, and by which the separated concentrated catalyst slurry may be effectively continuously and immediately recycled to the reaction zone, thereby to make the process more continuous than has been possible heretofore.

Since the average or mean particle size of the precursor material of the finely-divided magnesium silicate-supported complex cuprous acetylide catalyst ranges from about 1 to about 1,000 microns, usually from about 1 to about 200 microns, and the ethynylation reaction product mixture contains a high catalyst solids content, usually about 3 to about 30 weight % of the mixture, separation is difficult. Thus, while some filtering devices, such as a centrifuge, might be utilized to produce a high solids-catalyst recycle stream, centrifugation would not be able to produce a catalyst-free liquid product stream of sufficient clarity to be used directly in other operations. Moreover, while other continuous filter devices, such as a rotary drum filter, might produce the required clarity, such a filtration device would also produce a semi-solid catalyst that would have to be reslurried externally in a separate step, prior to recycle, a significant economic penalty.

For a separation means to satisfy the requirements of adequately removing the catalyst solids suspended in the reaction product mixture which is withdrawn from the reaction zone, for purposes of the present invention, such means has to meet at least the following rigid criteria: (1) it has to be capable of separating catalyst particles as small as those having a diameter of one micron; (2) it has to be capable of processing, safely, a catalyst-containing reaction product mixture that is saturated with acetylene; (3) it has to be capable of separating the mixture continuously into a catalyst-free or clear filtrate fraction, and a catalyst-containing fraction in the form of a flowable concentrated catalyst slurry that can be continuously and immediately recycled to the ethynylation reaction zone; (4) it must not deactivate the ethynylation catalyst during the separation process, for example, it must not induce acetylene starvation, which would cause the cuprous acetylide content of the catalyst to be reduced to elemental copper and be extracted in the filtrate, a potentially dangerous and explosive situation; and (5) it has to be capable of providing sufficient separation rates so as to provide favorable overall process economics.

SUMMARY OF THE INVENTION

In accordance with the objectives enumerated above, there is provided herein an improved, more continuous, low pressure ethynylation process for the production of butynediol which comprises first continuously reacting formaldehyde and acetylene in a reaction zone at low pressures, in a stirred aqueous medium, in the presence of a finely-divided ethynylation catalyst, to form a reaction product mixture containing butynediol and catalyst slurry. Then the reaction product mixture is withdrawn and continuously and simultaneously filtered and concentrated to form two streams, a catalyst-free filtrate stream and a flowable, concentrated catalyst slurry stream, the latter being capable of immediately recycling to reaction zone without further treatment. The filtrate stream containing the butynediol is available for purification and further operations.

DESCRIPTION OF THE INVENTION

DESCRIPTION OF THE PREFERRED EMBODIMENTS

Figure 1:
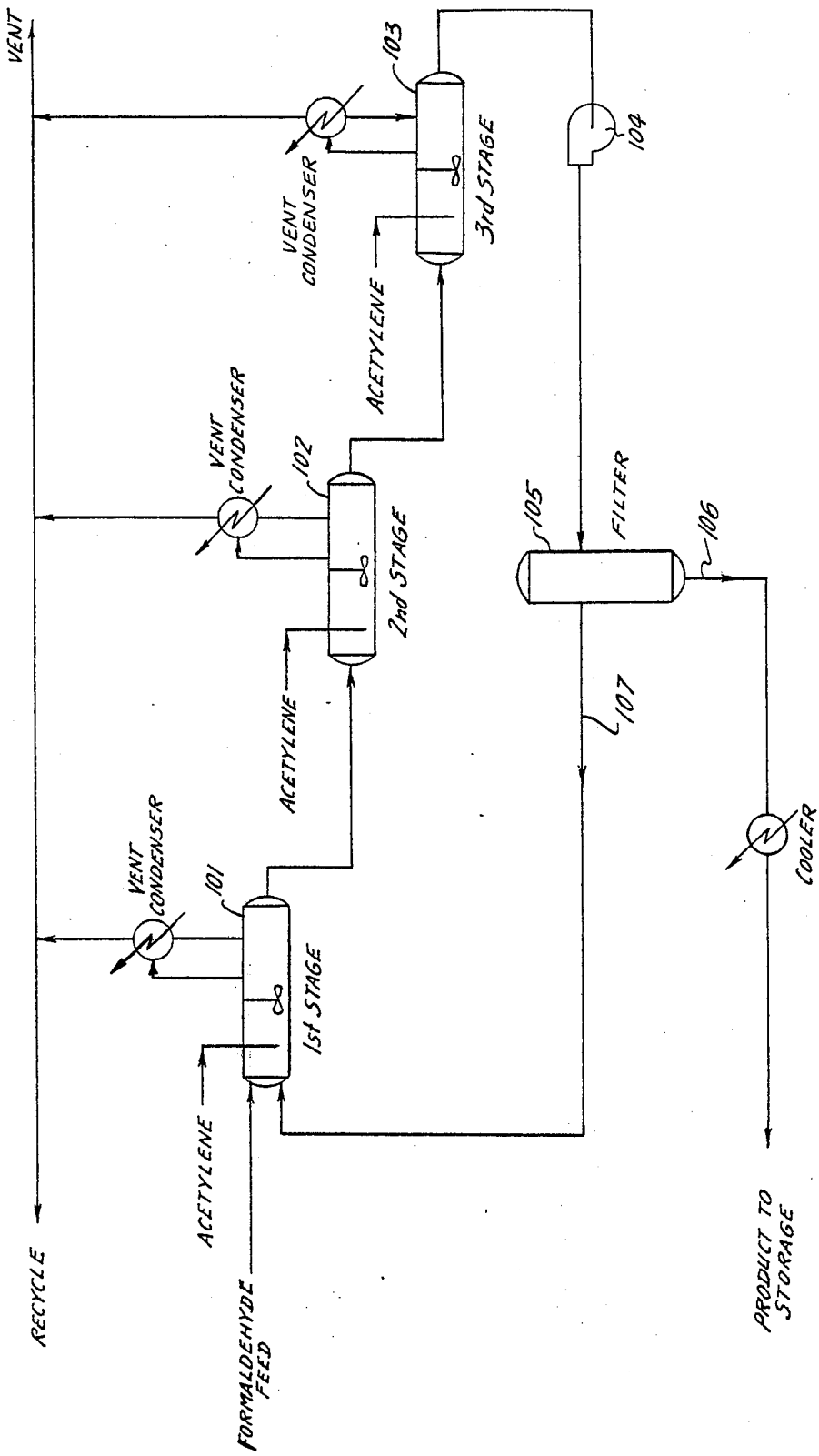
FIG. 1 is a schematic illustration of the improved continuous, low pressure ethynylation process for the production of butynediol in accordance with the teachings of the present invention.

Referring now to FIG. 1, there is shown suitable apparatus for carrying out the continuous, low pressure ethynylation process of the invention. As mentioned, the ethynylation reaction per se comprises reacting formaldehyde with acetylene in the presence of an ethynylation catalyst. Preferably the reaction is carried out at low pressures, i.e. a partial pressure of acetylene of less than 2 atmospheres, and at a suitable reaction temperature, usually at about 80° C. to about 110° C., in a stirred, aqueous medium in the presence of finely-divided, complex cuprous acetylide supported on magnesium silicate as a catalyst. The active catalyst is generated in situ from a catalyst precursor material which contains about 5—35% by weight copper, and, optionally, 0-3%, and, preferably, about 2-3% bismuth.

The ethynylation process may be carried out in batch fashion in a single reactor or it may be conducted in a series of connected reactors. Three in number are shown in FIG. 1, of approximately equal size. Each reactor is equipped with an efficient stirrer.

The reaction is commenced by pumping a suitable aqueous solution of formaldehyde, usually containing about 30–40% by weight formaldehyde, and admitting acetylene gas into the first reactor 101 containing the catalyst slurry at the prescribed temperature and pressure conditions. The reaction is continued to produce a reaction product which includes the desired butynediol. A small amount of propargyl alcohol usually formed as a by-product in the reaction is found also in the reaction product.

The reaction product and catalyst slurry then is continuously withdrawn from reactor 101 as a reaction product mixture and passed into reactor 102 (which is equivalent to a second stage). Further acetylene is introduced into the reaction product mixture obtained from reactor 101 to give a second mixture stream, which is then passed into reactor 103 (third stage). Meanwhile, the volatile matter passing upwards through the vent condensers can, optionally, either be vented to the atmosphere, or, preferably, recycled.

The reaction product mixture from the third stage or reactor 103 then is passed via pump 104 to the pressure filter and concentrator device, designated generally by reference numeral 105. Device 105 is adapted to continuously and simultaneously filter and concentrate the mixture to provide a catalyst-free filtrate stream 106 and a flowable, concentrated catalyst slurry stream 107. Filtrate 106 contains the desired butynediol together with small amounts of propargyl alcohol as by-product, and unreacted acetylene and formaldehyde. Stream 107 is immediately and continuously recycled without further treatment to the first stage, or reactor 101, together with fresh formaldehyde, thus providing a continuous process.

The catalyst-free filtrate 107 contains less than 25 ppm of solids. It may be used for further operations, or the butynediol recovered therefrom.

As described above, the pressure filtration and concentration device 105 provides a viable means of continuously and simultaneously separating the withdrawn reaction product mixture, containing fine catalyst particles, into a clarified product filtrate stream and a flowable, concentrated catalyst slurry stream, suitable for immediate and direct recycling to the reaction zone. In accordance therewith, a preferred device 105 is a pressure-leaf filter-concentrator which is shown more particularly in FIG. 2.

Figure 2:
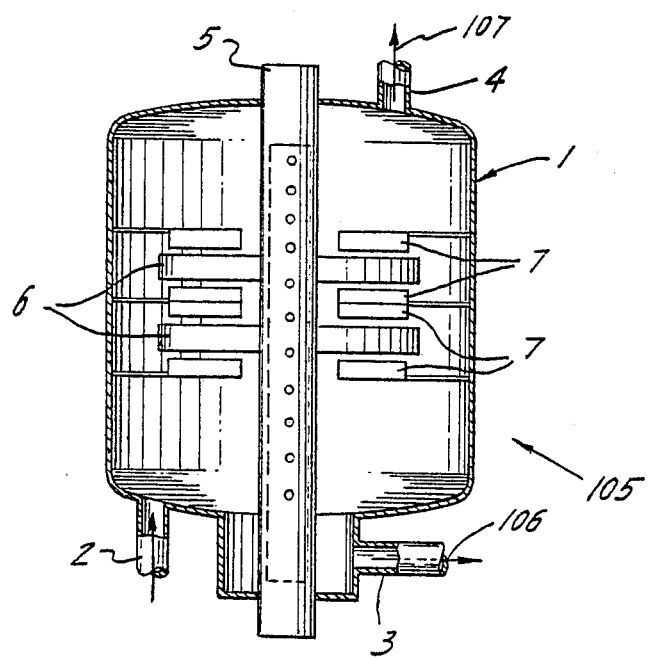
FIG. 2 is a view, partly in section, and partly diagrammatic, showing a vertically ranging pressure filter-concentrator device for the process of the invention.

The pressure filter-concentrator device of FIG. 2 includes a vessel 1 having an inlet 2 and at least two oppositely disposed outlets 3 and 4. A hollow perforated shaft 5 mounted to rotate within the vessel 1 has affixed to it filter elements 6. To the interior of vessel 1 is mounted scraper blades 7 which are positioned adjacent to the filter elements 6. During operation of the device, the reaction product mixture containing butynediol product, unreacted reactants and finely-divided catalyst slurry is introduced under pressure through inlet 2 where it is simultaneously filtered, concentrated, and separated into two streams by filter elements 6. One stream produced thereby is an essentially catalyst-free filtrate stream 106 which flows through the perforated hollow shaft 5 to the exterior of the vessel through outlet 3. The other stream is a concentrated catalyst stream 107 which has sufficient liquid therein to remain in a flowable slurry state. This catalyst stream is provided by the scraping action of blades 7 on any filter cake that build up on filter elements 6. Thereby, as solids build up on elements 6, they are continuously re-suspended to maintain a flowable slurry stream suitable for immediate recycling. The concentrated slurry is exited through outlet 4 and recycled.

A particularly useful form of filter and concentrator device 105 is the Schenk pressure-leaf filter-concentrator device, Model ZFE-40, sold by the Votator Division of Chemetron Corp., Louisville, Ky., although other similar equipment may be used as well.

The necessity of controlling the temperature at which the step of filtering and concentrating the withdrawn mixture is carried out will depend somewhat upon the composition of the catalyst used. Generally, the filtration temperature may range from 25°–130° C. In a preferred embodiment, however, separation is effected at temperatures within 20° C., and preferably within 10° C., of the ethynylation reaction temperature. A most preferred condition is to operate substantially at the reaction temperature.

If the separation step is carried out at too high a temperature, the rate of ethynylation between small amounts of acetylene and formaldehyde present in the withdrawn mixture will be increased. Thereby, acetylene available to the catalyst in the mixture will be depleted, inducing cuprous acetylide to precipitate, and increasing the possibility of an explosion. Accordingly, by operating within the prescribed temperature range, a partial pressure of acetylene is maintained in the separation device at all times.

A filtration temperature which is too low in device 105 is also undesirable. Although a low temperature would favor a decreased ethynylation rate therein, it would also reduce the viscosity of the liquid therein, and thus lower the throughput of the operation. Furthermore, plugging of the filtration medium may occur, owing to precipitation of silica that has been solubilized from the magnesium silicate during the course of the ethynylation reaction.

As stated, a preferred condition is to filter near the reaction temperature, which provides a high separation throughput, in the order of about 30–60 lbs. of clear filtrate per hr. per sq. ft. of filter area, without the difficulties mentioned.

The porosity of the filter layer (cloth) of device 105 is chosen as the maximum that will retain sufficient solids to build a thin layer filter cake quickly, thus preventing excessive solids from filtering through. Once established, the cake serves as the actual filter medium and results in excellent product clarity.

The degree of concentration of the outlet catalyst slurry 107 can be controlled by control of the inlet mixture rate and the operating pressure of the separator device 105. Alternatively, control of concentration may be effected by flow control of both outlet streams and throttling the inlet mixture flow to maintain the required filtration pressure. For economic considerations, it is usually desirable to maintain the solids content of the recycle catalyst stream at the maximum limits but sufficiently fluid for transport through the recycle ducts.

Increased average filtrate rates can be attained by occasional (approx. 6-8 hr. frequency) "backflush" of the filter elements. Backflushing is effected by (1) stopping the mixture feed, (2) relieving the filter pressure by bleeding pressure off through outlet duct 4, (3) forcing the filtrate in a reverse direction to normal flow through the filter elements to remove deposited cake, and (4) resuming the normal filtration mode. This backflushing can be accomplished in a matter of approximately five minutes. The backflushing operation, of course, can be readily automated, if desired.

Recycling of recovered, flowable, concentrated catalyst slurry to the reactor replaces substantially all the catalyst removed in the withdrawn effluent reaction mixture, providing a continuous, efficient process. However, the catalyst particles do get finer in time with continued use, and, organics may build up on the catalyst particles. Therefore, it is preferred that a small amount of catalyst in the reactor be removed daily (about 2%), and fresh catalyst substituted therefor.

The general operating conditions of the process of the invention is given below in Table I.

TABLE I
GENERAL OPERATING CONDITIONS

| | Practical Range | Preferred Range |
|---|---|---|
| Reaction Conditions | | |
| Temperature (° C.) | 80-110 | 85°-105 |
| Acetylene Partial Pressure (atm.) | Less than 2 | 0.4-1.5 |
| Catalyst Concentration (wt.%) | 3-30 | 5-15 |
| Catalyst Particle Size (microns) | 1-1,000 | 1-200 |
| Fresh Formaldehyde Feed Concentration (wt.% $CH_2O$) | 20-50 | 30-40 |
| Reactor Effluent Composition (Solids-Free Basis) (wt.%) | | |
| Butynediol | 20-60 | 35-50 |
| Formaldehyde | 0.1-10 | 0.5-3 |
| Propargyl Alcohol | 0.3-3 | 0.3-1.5 |
| Balance | Predominantly | Water |
| Filter-Concentrator Conditions | | |
| Pressure drop across elements (psi) | 10-100 | 30-60 |
| Temperature (° C.) | 25-130 | Within 10° C of Reaction Temperature |
| Filtrate Clarity (residual catalyst ppm) | 200 | 25 |
| Catalyst Content in recycle slurry concentrate (wt.%) | 10-40 | 25-35 |

The following examples will more fully illustrate the invention.

EXAMPLE 1

A three-stage, back-mixed, continuous butynediol process was carried out with the apparatus shown in FIGS. 1 and 2. The flow rates, compositions, and conditions specified below represent average values during a twenty-hour period, unless otherwise noted.

A finely-divided, supported, cuprous acetylidebismuth catalyst precursor material containing 14.1% copper and 2.46% bismuth was prepared by impregnating the metal nitrate salts onto a magnesium silicate powder carrier, drying and calcining, as described in U.S. Pat. No. 3,920,759. The particle size distribution of the precipitated catalyst precursor material is shown in Table II below.

TABLE II

| Particle Size | Fraction of Catalyst |
|---|---|
| Larger than 90 Microns | 37.6 Wt. % |
| 60 to 90 Microns | 1.81 Wt. % |
| 45 to 60 Microns | 1.32 Wt. % |
| 20 to 45 Microns | 5.27 Wt. % |
| 10 to 20 Microns | 14.0 Wt. % |
| Smaller than 10 Microns | 40.0 Wt. % |

The active catalyst then was generated in situ by reaction with formaldehyde and acetylene, also as described in U.S. Pat. No. 3,920,759.

Each reactor was maintained at 105° C., 13 psig total pressure and 9.7 psi acetylene partial pressure. Aqueous formaldehyde feed solution containing 31.6% formaldehyde was introduced into the first stage reactor at a controlled rate of 58.8 lbs/hr. In addition, the recycled concentrated catalyst slurry containing formaldehyde resulted in a net formaldehyde feed concentration of 10.7%. Constant levels were maintained in each reactor with continuous interstage flows.

On a continuous basis, the composition of the third stage reaction product mixture was 30.6% butynediol, 0.7% propargyl alcohol, 1.31% residual formaldehyde, the remainder being essentially water (on a solids-free basis), plus 10.8% catalyst solids. The third stage mixture was pumped at a rate of 208.3* lbs./hr. through the filter-concentrator device which was maintained at about 105° C. The device had four rotating filter plates which provided a combined filtration area of 2.2 sq. ft. A clearance of ⅛ inch was available between the surface of the filter plates and the set of stationary scraper blades. The unit was operated at 60 psig pressure on the slurry side and back-pressured on the filtrate side at an average of approximately 30 psig. The filter-concentrator device separated the third stage mixture into a sparkling clear (less than 25 ppm catalyst solids) product filtrate stream which was withdrawn to storage at a rate of 77.5 lbs./hr. or 35 lbs./hr.-ft.$^2$ mass flow through the filter elements. Concurrently, a concentrated flowable, catalyst slurry stream was obtained of the same liquid composition as the third stage reactor mixture plus 17.2% catalyst solids, at a stream flow rate of 130.8 lbs./hr. The flowable catalyst stream was continuously recycled to the first stage reactor.

*Water addition to the reactors average 11 lbs./hr., originating from equipment flushes, charging of small quantities of make-up catalyst, etc.

EXAMPLE 2

The final reaction product mixture from the low pressure, back-mixed reactor process, as described in Example I, contained 0.4 to 1.0% residual formaldehyde and 11.6 to 12.9% catalyst solids during a 26-hour test period. The particle size distribution of the catalyst solids was:

TABLE III

| Particle Size Diameter (Microns) | Cumulative Particles Smaller Than Indicated Size |
| --- | --- |
| 0.5 | 27 Wt. % |
| 1 | 43 Wt. % |
| 2 | 55 Wt. % |
| 5 | 82 Wt. % |
| 10 | 94 Wt. % |

The filter-concentrator produced a product filtrate stream of excellent clarity (no visible solids) at a rate of 77 lbs./hr. (35 lbs./hr.-ft.$^2$ mass flow rate) and a continuous recycle catalyst stream concentrated to 20.6–28.5% solids content.

EXAMPLE 3

Using a 22.7% copper, 2.5% bismuth catalyst with a particle size as in Example 1, a filtration rate at 95° C. (the same temperature as the reaction temperature) of 54 lbs./hr.-ft.$^2$ mass flow rate was obtained.

While the invention has been described with reference to certain embodiments thereof, it will be understood that changes and modifications may be made which are within the skill of the art. Accordingly, it is intended to be bound by the appended claims only.

What is claimed is:

1. A continuous, low pressure ethynylation process for the production of butynediol which comprises:
   (a) continuously reacting formaldehyde and acetylene in a reaction zone at a partial pressure of less than 2 atmospheres of acetylene and a reaction temperature of about 80° to about 110° C., in a stirred, aqueous medium, in the presence of a finely-divided ethynylation catalyst slurry, to form a reaction product liquid containing butynediol,
   (b) continuously withdrawing a mixture of said reaction product liquid and said catalyst slurry,
   (c) continuously and simultaneously filtering said mixture into a catalyst-free filtrate stream and a concentrate flowable catalyst slurry stream suitable for immediate recycling to said reaction zone, and,
   (d) continuously recycling said flowable, concentrated catalyst slurry stream to said reaction zone.

2. A process according to claim 1 wherein said ethynylation catalyst is a cuprous acetylide complex consisting essentially of about 5 to about 35% by weight of copper, and 0 to about 3% by weight bismuth supported on a magnesium silicate powder.

3. A process according to claim 1 wherein said recycled concentrated catalyst slurry provides a replacement for substantially all the catalyst withdrawn from said reaction zone.

4. A process according to claim 1 including the additional step of:
   (e) periodically removing a small amount of used catalyst and replacing it with about an equal amount of fresh catalyst.

5. A process according to claim 1 wherein said catalyst-free filtrate contains less than 25 ppm of said catalyst.

6. A process according to claim 1 wherein said flowable, concentrated catalyst slurry contains not more than about 40% by weight of catalyst.

7. A process according to claim 1 wherein the particle size of said catalyst is about 1–200 microns.

8. A process according to claim 1 wherein step (c) is carried out at a temperature of about 25°–130° C.

9. A process according to claim 1 wherein step (c) is carried out at a temperature within about 10° C. of the reaction temperature.

10. A continuous, multi-stage, low pressure ethynylation process for the production of butynediol which comprises:
    (a) continuously reacting formaldehyde and acetylene in a first stage reaction zone at a partial pressure of acetylene of less than 2 atmospheres and a reaction temperature of about 80° to 110° C., in a stirred, aqueous medium, in the presence of a finely-divided ethynylation catalyst slurry, to form a reaction product liquid containing butynediol,
    (b) continuously withdrawing a first stage mixture of said first stage reaction product and said catalyst slurry,
    (c) continuously passing said first stage mixture into a second stage reaction zone into which additional acetylene is being supplied,
    (d) repeating steps (b) and (c), if desired, to other additional reaction stages to produce a final stage reaction mixture,
    (e) continuously withdrawing said final stage reaction mixture,
    (f) continuously and simultaneously filtering said final stage mixture into a catalyst-free filtrate stream and a concentrated, flowable catalyst slurry stream suitable for immediate recycling to said first stage reaction zone, and
    (g) recycling said concentrated catalyst slurry to said first stage reaction zone.

11. A process according to claim 10 wherein said ethynylation catalyst is a cuprous acetylide complex consisting essentially of about 5 to about 35% by weight of copper, and 0 to about 3% by weight bismuth supported on a magnesium silicate powder.

12. A process according to claim 10 wherein said recycled concentrated catalyst slurry provides a replacement for substantially all the catalyst withdrawn from said reaction zone.

13. A process according to claim 10 including the additional step of:
    (h) periodically removing a small amount of used catalyst and replacing it with about an equal amount of fresh catalyst.

14. A process according to claim 10 wherein said catalyst-free filtrate contains less than 25 ppm of said catalyst.

15. A process according to claim 10 wherein said flowable, concentrated catalyst slurry contains not more than about 40% by weight of catalyst.

16. A process according to claim 10 wherein the particle size of said catalyst is about 1–200 microns.

17. A process according to claim 10 wherein step (f) is carried out at a temperature of about 25°–130° C.

18. A process according to claim 10 wherein step (f) is carried out at a temperature within about 10° C. of the reaction temperature.

* * * * *

REEXAMINATION CERTIFICATE (458th)
United States Patent [19]
Prater et al.

[11] B1 4,117,248
[45] Certificate Issued  Feb. 11, 1986

[54] CONTINUOUS, LOW PRESSURE ETHYNYLATION PROCESS FOR THE PRODUCTION OF BUTYNEDIOL

[75] Inventors: J. Lewis Prater, Calvert City, Ky.; Robert L. Hedworth, Kinnelon, N.J.

[73] Assignee: GAF Corporation, New York, N.Y.

Reexamination Request:
No. 90/000,758, Apr. 15, 1985

Reexamination Certificate for:
Patent No.: 4,117,248
Issued: Sep. 26, 1978
Appl. No.: 792,349
Filed: Apr. 29, 1977

[51] Int. Cl.$^4$ ............................................. C07C 29/00
[52] U.S. Cl. ..................................................... 568/855
[58] Field of Search ......................................... 568/855

[56] References Cited
U.S. PATENT DOCUMENTS

| | | | |
|---|---|---|---|
| 4,002,694 | 1/1977 | Hort | 568/874 |
| 4,067,914 | 1/1978 | Reiss et al. | 260/635 |

Primary Examiner—Joseph E. Evans

[57] ABSTRACT

There is provided herein an improved, more continuous, low pressure ethynylation process for the production of butynediol which comprises first continuously reacting formaldehyde and acetylene in a reaction zone at low pressures, in a stirred aqueous medium, in the presence of a finely-divided ethynylation catalyst, to form a reaction product mixture containing butynediol and catalyst slurry. Then the reaction product mixture is withdrawn and continuously and simultaneously filtered and concentrated to form two streams, a catalyst-free filtrate stream and a flowable, concentrated catalyst slurry stream, the latter being capable of immediate recycling to the reaction zone without further treatment. The filtrate stream containing the butynediol is available for purification and further operations.

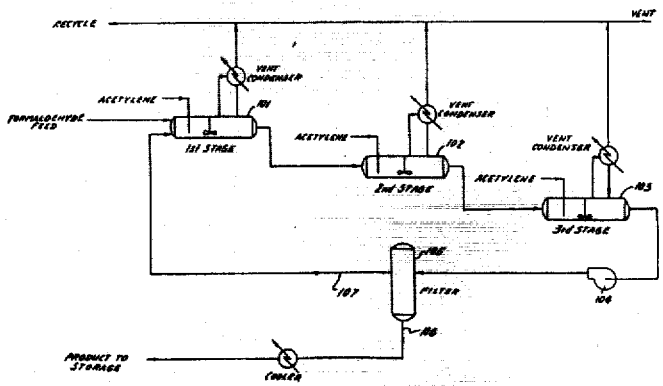

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–18 is confirmed.

New claims 19 and 20 are added and determined to be patentable.

*19. A process according to claim 1 wherein step (c) is carried out at a temperature within 20° C. of the reaction temperature.*

*20. A process according to claim 10 wherein step (f) is carried out at a temperature within 20° C. of the reaction temperature.*

* * * * *